United States Patent [19]

Banitt

[11] Patent Number: 4,491,584

[45] Date of Patent: Jan. 1, 1985

[54] ETHOXYPHENYL PIPERIDINES AND USES THEREOF

[75] Inventor: Elden H. Banitt, Woodbury, Minn.

[73] Assignee: Riker Laboratories, St. Paul, Minn.

[21] Appl. No.: 323,055

[22] Filed: Nov. 19, 1981

Related U.S. Application Data

[62] Division of Ser. No. 17,588, Mar. 5, 1979, abandoned, which is a division of Ser. No. 853,286, Nov. 21, 1977, Pat. No. 4,154,941, which is a division of Ser. No. 739,612, Nov. 8, 1976, Pat. No. 4,071,524.

[51] Int. Cl.$^3$ .................. C07D 211/26; C07D 211/28; A01N 31/44
[52] U.S. Cl. .................................... 424/263; 546/231; 568/587; 568/588; 564/442; 424/267; 548/567; 548/557
[58] Field of Search .................. 546/231; 260/326.47; 568/587, 588; 564/442; 424/263, 267; 548/557, 567

[56] References Cited

U.S. PATENT DOCUMENTS

| | | | |
|---|---|---|---|
| 3,937,726 | 2/1976 | Scherer et al. | 71/120 |
| 3,957,812 | 5/1976 | Rossignol et al. | 548/192 |
| 4,013,452 | 3/1977 | Scherer et al. | 71/120 |

*Primary Examiner*—Henry R. Jiles
*Assistant Examiner*—Robert C. Whittenbaugh
*Attorney, Agent, or Firm*—Donald M. Sell; James A. Smith; Donald C. Gipple

[57] ABSTRACT

Certain compounds in which a carbon atom of a pyrrolidine or piperidine ring is bonded directly or through a methylene group to the nitrogen of a phenyl-substituted urea, and their pharmaceutically acceptable salts, are active antiarrhythmic agents.

20 Claims, No Drawings

ETHOXYPHENYL PIPERIDINES AND USES THEREOF

This is a division of copending application Ser. No. 17,588 filed Mar. 5, 1979 now abandoned, Ser. No. 17,588 being a division of copending application Ser. No. 853,286, filed Nov. 21, 1977 (now U.S. Pat. No. 4,154,941), Ser. No. 853,286 being a division of copending application Ser. No. 739,612 filed Nov. 8, 1976 (now U.S. Pat. No. 4,071,524).

BACKGROUND OF THE INVENTION

This invention relates to certain compounds in which a carbon atom of a pyrrolidine or piperidine ring is bonded directly or through a methylene group of the N' nitrogen of an N-phenyl-substituted urea, and their pharmaceutically acceptable salts. The phenyl group of these compounds is substituted by one to three 1,1-dihydroperfluoroalkoxy substituents. The compounds and their pharmaceutically acceptable salts are active as antiarrhythmic agents. The invention also relates to certain novel intermediates and to processes useful to prepare the compounds.

No urea derivatives structurally analogous to the compounds of this invention are known in the art. Local anesthetic activity has been reported by Koelzer and Wehr, Arzneim. Forsch., 8, 664 (1958) for N-(alkylamino)-N'-phenylureas wherein the phenyl ring is substituted by halogen or lower alkyl.

Esters of benzoic acid substituted on the aromatic ring by 1,1-dihydroperfluoroalkoxy substituents are described in U.S. Pat. No. 3,655,728. Certain amides of benzoic acid substituted on the aromatic ring by 1,1-dihydroperfluoroalkoxy substituents are described in U.S. Pat. No. 3,719,687. Other amides of benzoic acid substituted on the aromatic ring by 1,1-dihydroperfluoroalkoxy substituents are described in U.S. Pat. No. 3,900,481.

DETAILED DESCRIPTION OF THE INVENTION

This invention relates to chemical compounds and their pharmaceutically acceptable salts, processes for using the compounds of the invention, pharmaceutical compositions containing the compounds, processes for the preparation of the compounds and novel intermediates useful in the processes of the invention.

The free base compounds of the invention are broadly described as follows:

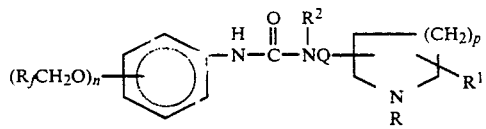

I wherein $R_f$ is a perfluoroalkyl radical containing one to three carbon atoms ($C_mF_{2m+1}$ where m is 1-3), n is one to three, p is one or two, Q is a carbon-nitrogen bond, methylene (—CH$_2$—), or methylmethylene (—CH(CH$_3$)—), R and $R^1$ are hydrogen, methyl or ethyl, and $R^2$ is lower alkyl or hydrogen, provided that when Q is a carbon-nitrogen bond it is bonded to the 3 position of the heterocyclic ring and when it is methylene or methylmethylene it is bonded to the 2 position. The term "lower" whenever used herein relative to a substituent denotes a group containing from one to four carbon atoms. The notation as to the various symbols (e.g. $R_f$, n, $R^2$, Q, etc.) is uniform throughout this specification unless otherwise specifically stated.

Presently preferred are compounds of the invention wherein Q is a methylene or methylmethylene linking group and is bonded to the 2 position of the pyrrolidine or piperidine ring. These compounds are preferred because of generally greater antiarrhythmic potency as detected by animal tests.

Compounds of the invention wherein n is two, $R_f$ is $CF_3$ and the orientation of the dihydroperfluoroethoxy groups is 2,5 are also a presently preferred class.

The compounds of the invention have at least one asymmetric carbon (the carbon atom of the pyrrolidine or piperidine ring to which the group Q is bonded) and can be resolved into optically active enantiomers by methods known to the art. In addition, other asymmetric centers are possible, e.g. when Q is methylmethylene or $R^1$ is methyl or ethyl. All of these optical isomers are included within the scope of the invention.

The compounds can be used directly or in the form of pharmaceutically acceptable acid-addition salts, especially as soluble acetic, hydrochloric, sulfuric or phosphoric acid salts. Other such salts include combinations with hydrobromic acid, sulfamic acid, methanesulfonic acid, benzenesulfonic acid, ethanedisulfonic acid, citric acid, maleic acid, oxalic acid, succinic acid, malic acid, fumaric acid and tartaric acid. Pharmaceutically acceptable quaternary ammonium salts are also used, for example alkyl (especially lower alkyl) iodide and bromide salts.

The compounds of the invention are generally active as antiarrhythmics, although both the activity (exhibited by the test methods presently available) and the therapeutic indices vary from compound to compound. The antiarrhythmic activity of compounds is manifested in their ability to block chloroform-induced ventricular fibrillation in mice, as demonstrated by the test procedure described in detail by J. W. Lawson, J. Pharmacol. Exp. Therap. 160:22–31, 1966.

Presently preferred compounds of the invention having high antiarrhythmic activity are:

N-[2,5-bis(2,2,2-trifluoroethoxy)phenyl]-N'-(2-piperidyl)methylurea,

N-[2,5-bis(2,2,2-trifluoroethoxy)phenyl]-N'[1-(2-piperidyl)ethyl]urea and pharmaceutically acceptable salts thereof.

In clinical practice, the derivatives of the invention will normally be administered as antiarrhythmics orally or by injection in the form of pharmaceutical preparations comprising the active ingredient in the form of the free base or one of the common therapeutically acceptable salts, e.g., the acetate or hydrochloride, in association with a pharmaceutically acceptable carrier. The carrier may be a solid, semi-solid or liquid diluent or an ingestible capsule. Usually the active substance will comprise between 0.01 percent and 5 percent of preparations intended for injection and between 10 percent and 80 percent of preparations intended for oral administration. Particularly preferred for intravenous use are 0.05–1.0 percent aqueous solutions of the active compounds buffered with sodium acetate to pH of about 5–7 and, for oral use, 20–60 percent formulations of the active ingredient in mannitol, lactose or potato starch.

Pharmaceutical preparations in the form of dosage units for oral administration containing a compound of the invention in the form of the free base or a pharmaceutically acceptable acid addition salt may be prepared in various ways. The compounds may be mixed with a solid, pulverulent carrier, for example lactose, saccharose, sorbital, mannitol, starches such as potato starch, corn starch or amylopectin, cellulose derivatives, gelatin. The carrier may also be a lubricant such as magnesium or calcium stearate, a Carbowax or other polyethylene glycol wax compressed to form tablets or, preferably, cores which are then coated with a concentrated sugar solution which may contain, e.g., gum arabic, gelatin, talcum and/or titanium dioxide.

Ingestible capsules which may be used include hard and soft gelatin capsules. Soft gelatin capsules (pearl-shaped closed capsules) and other closed capsules consist, for example, of a mixture of gelatin and glycerol, and contain, e.g., mixtures of the active substance with a vegetable oil, and hard gelatin capsules contain, for example, granulates of the active substance with solid, pulverulent carriers such as lactose, saccharose, sorbitol, mannitol; starches such as potato starch, corn starch or amylopectin; cellulose derivatives or gelatin, as well as magnesium stearate or stearic acid.

For parenteral application by injection the preparations of the invention advantageously comprise an aqueous, generally saline, solution of a water-soluble, pharmaceutically acceptable salt of the active substance and optionally also a stabilizing agent and/or a buffer substance, e.g. sodium acetate.

The antiarrhythmic compounds of the invention can be prepared by reacting an isocyanate of the formula:

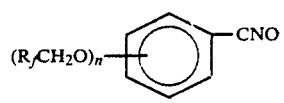

II wherein $R_f$ and n are as defined hereinabove, with an amine of the formula

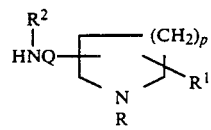

III wherein $R^2$, Q, R, $R^1$ and p are as previously defined, except that when Q is in the 2 position it is not a carbon-nitrogen bond. The reaction is carried out in an inert solvent such as chloroform, dichloromethane, glyme, toluene, diethyl ether and the like. The reaction temperature is from about 0° C. to the reflux temperature of the solvent, depending upon the reactivity of the amine utilized. Preferably R is not hydrogen, since it would react competitively with the desired reaction site and produce a mixture from which the desired product must be separated. Isolation of the product is readily carried out by conventional methods.

In order to prepare compounds wherein R is hydrogen and p is two, it is preferable to react the isocyanate with an amine of the formula

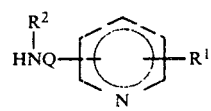

IV wherein $R^2$, Q and $R^1$ are as previously defined, to provide a novel intermediate of the formula

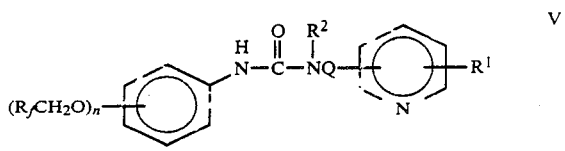

V which is subsequently selectively reduced to form the desired product of the invention. Reduction of the intermediate V is carried out readily with pyridine derivatives using platinum oxide as catalyst. The reduction will generally be carried out in a solvent such as methanol or acetic acid.

The isocyanate intermediates (II) are also novel. They are prepared from the corresponding amines:

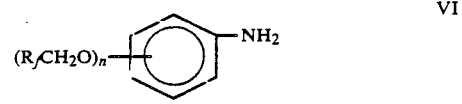

VI by reaction with phosgene in an inert solvent such as toluene by gradually heating the reaction mixture to a temperature at which reaction occurs, monitoring the reaction until complete and evaporating the solvent and volatile byproducts to provide the product isocyanate.

The amines (VI) are prepared by reduction of the corresponding nitro compounds:

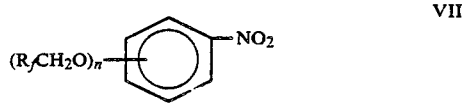

VII using chemical or catalytic reduction. It has been found that Raney nickel is a particularly convenient catalyst, providing very high yields. The solvents used are non-reactive to the reaction conditions such as ethanol and methanol.

The amines (VI) and the nitro compounds (VII) are also novel and form aspects of the present invention. In these compounds, the values of $R_f$ and n are also as previously stated.

The nitro compounds (VII) are readily prepared from known compounds. All of the six isomeric dihydroxynitrobenzenes are known, and they are readily polyfluoroalkylated, for example trifluoroethylated, to provide the desired nitrobis(2,2,2-trifluoroethyoxy)benzenes. Mono- and trihydroxynitrobenzenes can also be polyfluoroalkylated.

Alternatively some of the isomeric polyfluoroalkylated intermediates such as nitrobis(2,2,2-trifluoroethoxy)-benzenes, for example, 2,5-bis(2,2,2-trifluoroethoxy)nitrobenzene and 2,4-bis(2,2,2-trifluorethoxy)nitrobenzene are synthesized by nitration of 1,4-bis(2,2,2-trifluoroethoxy)benzene and 1,3-bis(2,2,2-trifluoroethoxy)benzene, respectively. This nitration is readily carried out by addition of about one equivalent of nitric acid to a trifluoroacetic acid solution of the benzene derivative.

The following examples will more fully illustrate the preparation of the compositions of the invention. All temperatures in the examples are given in degrees Centigrade.

EXAMPLE 1

To 58.1 g. (0.212 mole) of 1,4-bis(2,2,2-trifluoroethoxy)benzene in 400 ml. of trifluoroacetic acid is added dropwise with stirring 13.7 ml. of concentrated nitric acid over 3.5 hours at 25°±2° C. Stirring is continued for 24 hours, then the mixture is concentrated to one-third the original volume. The concentrate is poured into 600 ml. of water, and the resulting solution is extracted twice with diethyl ether. The ether solution is washed thrice with saturated sodium chloride solution, then with dilute sodium hydroxide solution until the washings are basic. The solution is washed again with saturated sodium chloride solution, dried and evaporated. The liquid residue is distilled to provide 2,5-bis(2,2,2-trifluoroethoxy)nitrobenzene as a clear, pale yellow liquid, b.p. 116°–119° C./0.35 mm Hg.

EXAMPLE 2

To a refluxing mixture of 12.7 g (0.092 mole) of potassium carbonate, 21.3 g. (0.092 mole) of 2,2,2-trifluoroethyl trifluoromethanesulfonate and 62 ml. of acetone is added dropwise 6.2 g. (0.040 mole) of 4-nitrocatechol in 62 ml. of acetone over about 2.5 hours. Refluxing is continued for a total of 24 hours, then the solution is evaporated. The residue is mixed with equal volumes of water and diethyl ether. The ether layer is separated, washed with water and saturated sodium chloride solution and dried. Evaporation provides crude 3,4-bis(2,2,2-trifluoroethoxy)nitrobenzene. Chromatographic purification on a silica gel column is effected by eluting with mixtures of chloroform and hexane. Recrystallization from cyclohexane with a small amount of benzene provides solid product, m.p. 63°–65° C.

| Analysis: | % C | % H | % N |
|---|---|---|---|
| Calculated for $C_{10}H_7F_6NO_4$: | 37.6 | 2.2 | 4.4 |
| Found: | 37.5 | 2.2 | 4.3 |

Using the method of Example 2 the following intermediate compounds are prepared.

TABLE I

| Ex. No. | Starting Material | Product |
|---|---|---|
| 3 | 2-nitrocatechol (1,2-dihydroxy-3-nitrobenzene) | 1,2-bis(OCH$_2$CF$_3$)-3-nitrobenzene |
| 4 | 2-nitroresorcinol (1,3-dihydroxy-2-nitrobenzene) | 1,3-bis(OCH$_2$CF$_3$)-2-nitrobenzene |
| 5 | 4-nitroresorcinol (1,3-dihydroxy-4-nitrobenzene) | 1,3-bis(OCH$_2$CF$_3$)-4-nitrobenzene |
| 6 | 5-nitroresorcinol (1,3-dihydroxy-5-nitrobenzene) | 1,3-bis(OCH$_2$CF$_3$)-5-nitrobenzene |
| 7 | 2-nitrophenol | 1-(OCH$_2$CF$_3$)-2-nitrobenzene |
| 8 | 1,2,4-trihydroxy-5-nitrobenzene | 1,2,4-tris(OCH$_2$CF$_3$)-5-nitrobenzene |

EXAMPLE 9

A mixture of 59 g. (0.185 mole) of 2,5-bis-(2,2,2-trifluoroethoxy)nitrobenzene, about 15 g. of Raney nickel and 1200 ml. of ethanol is hydrogenated by shaking on a Parr hydrogenation apparatus with a hydrogen pressure of 40 to 50 p.s.i. for about five hours. The mixture is filtered, and the filtrate is evaporated to a liquid residue. The residue is distilled to provide 2,5-bis(2,2,2-trifluoroethoxy)aniline as a clear, colorless liquid, b.p. 95°–98° C./0.35 mm Hg.

EXAMPLE 10

Using the method of Example 9 and starting with 3,4-bis(2,2,2-trifluoroethoxy)nitrobenzene the product obtained is 3,4-bis(2,2,2-trifluoroethoxy)aniline, b.p. 96°–102° C./0.2 mm Hg.

| Analysis: | % C | % H | % N |
|---|---|---|---|
| Calculated for $C_{10}H_9F_6NO_2$: | 41.5 | 3.1 | 4.8 |
| Found: | 41.5 | 3.1 | 4.7 |

Using the method of Example 9 the following intermediate compounds are prepared.

TABLE II

| Ex. No. | Starting Material | Product |
|---|---|---|
| 11 | 1,2-bis(OCH$_2$CF$_3$)-3-nitrobenzene | 1,2-bis(OCH$_2$CF$_3$)-3-aminobenzene |
| 12 | 1,3-bis(OCH$_2$CF$_3$)-2-nitrobenzene | 1,3-bis(OCH$_2$CF$_3$)-2-aminobenzene |
| 13 | 1,3-bis(OCH$_2$CF$_3$)-4-nitrobenzene | 1,3-bis(OCH$_2$CF$_3$)-4-aminobenzene |
| 14 | 1,3-bis(OCH$_2$CF$_3$)-5-nitrobenzene | 1,3-bis(OCH$_2$CF$_3$)-5-aminobenzene |
| 15 | 1-(OCH$_2$CF$_3$)-2-nitrobenzene | 1-(OCH$_2$CF$_3$)-2-aminobenzene |

TABLE II-continued

| Ex. No. | Starting Material | Product |
|---|---|---|
| 16 | 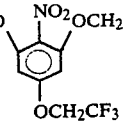 | 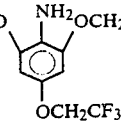 |

EXAMPLE 17

To a cooled (15°–20° C.) solution of 67.6 g. (0.684 mole) of phosgene in 250 ml. of toluene is added dropwise over one hour a solution of 49.5 g. (0.171 mole) of 2,5-bis-(2,2,2-trifluoroethoxy)aniline in 350 ml. of toluene. After addition is complete, stirring is continued for 30 minutes, then the mixture is heated to its reflux temperature and maintained at reflux for 30 minutes. The solution is evaporated to provide a liquid residue which gradually crystallizes. The solid is recrystallized from heptane to provide 2,5-bis(2,2,2-trifluoroethoxy)phenyl isocyanate as a white solid, m.p. 50°–52° C.

EXAMPLE 18

Using the method of Example 17 and starting with 3,4-bis(2,2,2-trifluoroethoxy)aniline, 3,4-bis(2,2,2-trifluoroethoxy)phenyl isocyanate, m.p. 53°–55° C., is obtained after recrystallization from petroleum ether.

| Analysis: | % C | % H | % N |
|---|---|---|---|
| Calculated for $C_{11}H_7F_6NO_3$: | 41.9 | 2.2 | 4.45 |
| Found: | 41.5 | 2.2 | 4.4 |

Using the method of Example 17 the following intermediate compounds are prepared.

TABLE III

| Ex. No. | Starting Material | Product |
|---|---|---|
| 19 | 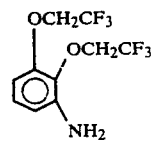 | 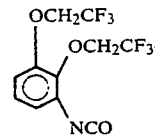 |
| 20 | 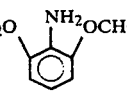 | 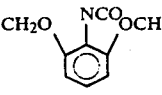 |
| 21 | 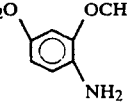 | 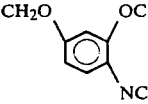 |
| 22 | 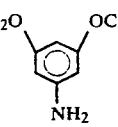 | 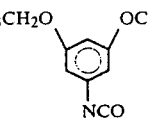 |
| 23 | 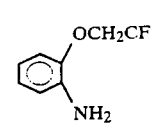 | 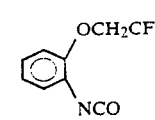 |
| 24 | 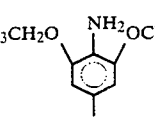 | 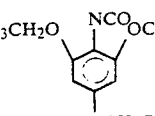 |

EXAMPLE 25

Step A

To a solution of 2.7 g. (0.020 mole) of methyl-2-(6-methylpyridyl)methylamine in 63 ml. of chloroform is added dropwise over 2.5 hours 6.3 g. (0.020 mole) of 2,5-bis(2,2,2-trifluoroethoxy)phenyl isocyanate. The mixture is stirred for two hours, then heated to reflux and maintained at reflux for two hours. The solution is evaporated to provide an oil as the residue. The oil is dissolved in ethyl acetate, and 3.0 ml. of 7M isopropanolic hydrogen chloride is added. The product is separated by filtration to give N-[2,5-bis(2,2,2-trifluoroethoxy)phenyl]-N'-methyl-N'-[2-(6-methylpyridyl)methyl]urea hydrochloride, m.p. 164°–166.5° C.

Step B

A mixture of 9.3 g. (0.0195 mole) of the urea (used as the hydrochloride salt) from Step A, 0.3 g. of platinum oxide and 250 ml. of methanol is hydrogenated by shaking on a Parr hydrogenation apparatus with a hydrogen pressure of 44 to 50 p.s.i. The mixture is then filtered and the filtrate is evaporated. The residue is recrystallized from acetonitrile to provide N-[2,5-bis(2,2,2-trifluoroethoxy)phenyl]-N'-methyl-N'-[2-(6-methylpiperidyl)methyl]urea hydrochloride, m.p. 203°–205.5° C.

| Analysis: | % C | % H | % N |
|---|---|---|---|
| Calculated for $C_{19}H_{25}F_6N_3O_3$·HCl: | 46.2 | 5.3 | 8.5 |
| Found: | 46.0 | 5.2 | 8.4 |

Using the general method of Example 25 except using acetic acid as solvent in the hydrogenation step and starting with 2,5-bis(2,2,2-trifluoroethoxy)phenyl isocyanate and the various amines shown, the compounds of Table IV are prepared. The figures given beneath the formulae in the intermediate and final product columns in the table are the melting points of the respective compounds in degrees centigrade.

TABLE IV

| Example No. | Amine Starting Material | Intermediate | Final Product |
|---|---|---|---|
| 26 | 2-pyridyl-CH₂NH(CH₂)₃CH₃ | 2,5-bis(OCH₂CF₃)-C₆H₃-NHC(O)N((CH₂)₃CH₃)-CH₂-(2-pyridyl) | 2,5-bis(OCH₂CF₃)-C₆H₃-NHC(O)N((CH₂)₃CH₃)-CH₂-(2-piperidyl)·HCl, 168–169.5 |
| 27 | 2-pyridyl-CH₂NHCH₃ | 2,5-bis(OCH₂CF₃)-C₆H₃-NHC(O)N(CH₃)-CH₂-(2-pyridyl)·HCl, 145–146 | 2,5-bis(OCH₂CF₃)-C₆H₃-NHC(O)N(CH₃)-CH₂-(2-piperidyl)·CH₃COOH, 110–112 |
| 28 | 2-pyridyl-CH₂NH₂ | 2,5-bis(OCH₂CF₃)-C₆H₃-NHC(O)NHCH₂-(2-pyridyl), 140–141.5; hydrochloride 182–184 | 2,5-bis(OCH₂CF₃)-C₆H₃-NHC(O)NHCH₂-(2-piperidyl)·HCl, 194–195 |
| 29 | 2-pyridyl-CH(CH₃)NH₂ | 2,5-bis(OCH₂CF₃)-C₆H₃-NHC(O)NHCH(CH₃)-(2-pyridyl) | 2,5-bis(OCH₂CF₃)-C₆H₃-NHC(O)NHCH(CH₃)-(2-piperidyl)·FUMARIC ACID, 198–199 |
| 30 | 3-aminopyridine | 2,5-bis(OCH₂CF₃)-C₆H₃-NHC(O)NH-(3-pyridyl), 171–173 | 2,5-bis(OCH₂CF₃)-C₆H₃-NHC(O)NH-(3-piperidyl)·CH₃CO₂H, 146–147 |

Using the general method illustrated in Example 25 and starting with various isocyanates shown and 2-(aminomethyl)pyridine the following compounds of the invention are prepared.

TABLE V

| Example No. | Isocyanate Starting Material | Intermediate | Product |
|---|---|---|---|
| 31 | 2,3-bis(OCH₂CF₃)-C₆H₃-NCO | 2,3-bis(OCH₂CF₃)-C₆H₃-NHC(O)NHCH₂-(2-pyridyl) | 2,3-bis(OCH₂CF₃)-C₆H₃-NHC(O)NHCH₂-(2-piperidyl) |
| 32 | 2,6-bis(OCH₂CF₃)-C₆H₃-NCO | 2,6-bis(OCH₂CF₃)-C₆H₃-NHC(O)NHCH₂-(2-pyridyl) | 2,6-bis(OCH₂CF₃)-C₆H₃-NHC(O)NHCH₂-(2-piperidyl) |

TABLE V-continued

| Example No. | Isocyanate Starting Material | Intermediate | Product |
|---|---|---|---|
| 33 | 2,5-bis(2,2,2-trifluoroethoxy)-4-(2,2,2-trifluoroethoxy)phenyl isocyanate | N-[2,5-bis(2,2,2-trifluoroethoxy)-4-(2,2,2-trifluoroethoxy)phenyl]-N'-[(pyridin-2-yl)methyl]urea | N-[2,5-bis(2,2,2-trifluoroethoxy)-4-(2,2,2-trifluoroethoxy)phenyl]-N'-[(piperid-2-yl)methyl]urea |
| 34 | 3,5-bis(2,2,2-trifluoroethoxy)phenyl isocyanate | corresponding pyridylmethyl urea | corresponding piperidylmethyl urea |
| 35 | 2-(2,2,2-trifluoroethoxy)phenyl isocyanate | corresponding pyridylmethyl urea | corresponding piperidylmethyl urea |
| 36 | 2,4,6-tris(2,2,2-trifluoroethoxy)phenyl isocyanate | corresponding pyridylmethyl urea | corresponding piperidylmethyl urea |

EXAMPLE 37

To a solution of 1.35 g. (0.0095 mole) of 2-(1-ethyl-piperidyl)methylamine in 14 ml. of chloroform is added dropwise 3.0 g. of 2,5-bis(2,2,2-trifluoroethoxy)phenyl isocyanate in 30 ml. of chloroform over 75 minutes. The mixture is heated to reflux and maintained at reflux for two hours. The mixture is then concentrated to give a solid residue. The residue is dissolved in diethyl ether and treated with diethyl ether saturated with fumaric acid to provide N-[2,5-bis(2,2,2-trifluoroethoxy)-phenyl]-N'-[(1-ethylpiperid-2-yl)methyl]urea fumarate, m.p. 156°–161° C.

| Analysis: | % C | % H | % N |
|---|---|---|---|
| Calculated for $C_{19}H_{25}F_6N_3O_3 \cdot 0.6 C_4H_4O_4$: | 48.7 | 5.2 | 8.0 |
| Found: | 49.0 | 5.3 | 8.0 |

EXAMPLE 38

To a solution of 1.28 g. (0.010 mole) of 2-(1-methyl-piperidyl)methylamine in 26 ml. of chloroform is added dropwise over one hour 3.15 g. (0.010 mole) of 2,5-bis(2,2,2-trifluoroethoxy)phenyl isocyanate in 32 ml. of chloroform. The mixture is heated to reflux and maintained at reflux for two hours. The mixture is then concentrated to give a solid which is recrystallized from cyclohexane and a little benzene to provide N-[2,5-bis(2,2,2-trifluoroethoxy)phenyl]-N'-[(1-methylpiperid-2-yl)methyl]urea, m.p. 123°–126° C.

| Analysis: | % C | % H | % N |
|---|---|---|---|
| Calculated for $C_{18}H_{23}F_6N_3O_3$: | 48.8 | 5.2 | 9.5 |
| Found: | 48.8 | 5.0 | 9.6 |

EXAMPLE 39

Using the method of Examples 37 and 38, 2,5-bis(2,2,2-trifluoroethoxy)phenyl isocyanate is reacted with N-ethyl-2-(1-methylpyrrolidinyl)methylamine in chloroform to provide N-[2,5-bis(2,2,2-trifluoroethoxy)phenyl]-N'-ethyl-N'-[(1-methylpyrrolidin-2-yl)methyl]urea, b.p. 165° C./0.13 mm Hg.

| Analysis: | % C | % H | % N |
|---|---|---|---|
| Calculated for $C_{19}H_{25}F_6N_3O_3$: | 49.9 | 5.5 | 9.2 |
| Found: | 49.3 | 5.3 | 8.9 |

EXAMPLE 40

Using the method of Examples 37 and 38, 3,4-bis(2,2,2-trifluoroethoxy)phenyl isocyanate is reacted with 2-(1-ethylpiperidyl)methylamine in chloroform to provide N-[3,4-bis(2,2,2-trifluoroethoxy)phenyl]-N'-[(1-ethylpiperid-2-yl)methyl]-urea as an oil.

| Analysis: | % C | % H | % N |
|---|---|---|---|
| Calculated for $C_{19}H_{25}F_6N_3O_3$: | 49.89 | 5.5 | 9.2 |
| Found: | 49.4 | 5.5 | 9.0 |

EXAMPLE 41

A sample of N-[2,5-bis(2,2,2-trifluoroethoxy)phenyl]-N'-ethyl-N'-[(1-methylpyrrolidin-2-yl)methyl]urea is dissolved in diethyl ether and treated with an ether solution of an equimolar amount of fumaric acid to provide a solid which is separated by filtration. The product is recrystallized from ethyl acetate to provide N-[2,5-bis(2,2,2-trifluoroethoxy)phenyl]-N'-ethyl-N'-[(1-methylpyrrolidin-2-yl)methyl]urea fumarate, m.p. 138° C. (dec.).

| Analysis: | % C | % H | % N |
|---|---|---|---|
| Calculated for C₁₉H₂₅N₃O₃.C₄H₄O₄: | 48.2 | 5.1 | 7.3 |
| Found: | 47.9 | 5.2 | 7.2 |

What is claimed is:

1. A method for treatment and prevention of arrhythmias comprising administering an effective dose less than the toxic amount of a compound of the formula

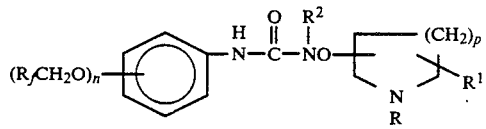

wherein $R_f$ is a perfluoroalkyl radial containing one to three carbon atoms, n is one to three, p is one or two, Q is a carbon-nitrogen bond, methylene or methylmethylene, R and $R^1$ are hydrogen, methyl or ethyl, and $R^2$ is lower alkyl or hydrogen, provided that when Q is a carbon-nitrogen bond it is bonded to the 3 position of the heterocyclic ring and when it is methylene or methylmethylene it is bonded to the 2 position of the heterocyclic ring, and pharmaceutically acceptable salts thereof.

2. A method according to claim 1 wherein n is 2.
3. A method according to claim 1 wherein p is 2.
4. A method according to claim 1 wherein $R^2$ is hydrogen.
5. A method according to claim 1 wherein $R_f$ is trifluoromethyl.
6. A method according to claim 1 wherein n is 2 and $R_f$ is trifluoromethyl.
7. A method according to claim 1 wherein the compound is N-[2,5-bis(2,2,2-trifluoroethoxy)phenyl]-N'-(2-piperidyl)methylurea or a salt thereof.
8. A method according to claim 1 wherein the compound is N-[2,5-bis(2,2,2-trifluoroethoxy)phenyl]-N'-(2-piperidyl)-ethyl)urea or a salt thereof.
9. A compound of the formula

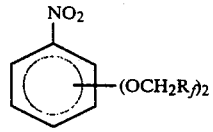

wherein $R_f$ is a perfluoroalkyl radical containing one to three carbon atoms.

10. A compound of the formula

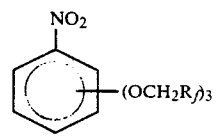

wherein $R_f$ is a perfluoroalkyl radical containing one to three carbon atoms.

11. A compound according to claim 9, wherein $R_f$ is trifluoromethyl.
12. A compound according to claim 10, wherein $R_f$ is trifluoromethyl.
13. A compound according to claim 9, of the formula

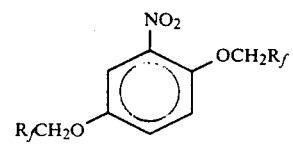

14. The compound 2,5-bis(2,2,2-trifluoroethoxy)nitrobenzene according to claim 13.
15. A compound of the formula

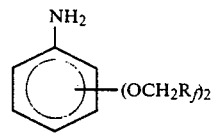

wherein $R_f$ is a perfluoroalkyl radical containing one to three carbon atoms.

16. A compound of the formula

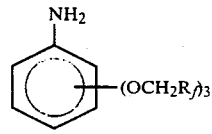

wherein $R_f$ is a perfluoroalkyl radical containing one to three carbon atoms.

17. A compound according to claim 15 wherein $R_f$ is trifluoromethyl.
18. A compound according to claim 16 wherein $R_f$ is trifluoromethyl.
19. A compound according to claim 15 of the formula

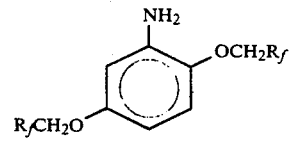

20. The compound 2,5-bis(2,2,2-trifluoroethoxy)aniline according to claim 19.

* * * * *